US00PP18264P2

(12) United States Plant Patent
Kievit

(10) Patent No.: US PP18,264 P2
(45) Date of Patent: Dec. 4, 2007

(54) ***FUCHSIA* PLANT NAMED 'KIEFUCOR'**

(50) Latin Name: *Fuchsia×hybrida*
Varietal Denomination: Kiefucor

(75) Inventor: Christa Kievit, Hem (NL)

(73) Assignee: Kieft Bloemzaden B.V., Venhuizen (NL)

( * ) Notice: Subject to any disclaimer, the term of this patent is extended or adjusted under 35 U.S.C. 154(b) by 0 days.

(21) Appl. No.: 11/450,831

(22) Filed: Jun. 9, 2006

(51) Int. Cl.
*A01H 5/00* (2006.01)

(52) U.S. Cl. ..... Plt./300
(58) Field of Classification Search ..... Plt./300
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Fuchsia* plant named 'Kiefucor', characterized by its outwardly arching to trailing growth habit; freely branching plant habit; white-colored flowers; and freely and continuous flowering habit.

1 Drawing Sheet

Botanical designation: *Fuchsia×hybrida.*
Cultivar denomination: 'Kiefucor'.

BACKGROUND OF THE INVENTION

The present invention relates to a new and distinct cultivar of *Fuchsia,* botanically known as *Fuchsia×hybrida* and hereinafter referred to by the name 'Kiefucor'.

The new *Fuchsia* is a product of a planned breeding program conducted by the Inventor in Venhuizen, The Netherlands. The objective of the breeding program is to create new outwardly arching *Fuchsia* cultivars with numerous flowers and attractive flower coloration.

The new *Fuchsia* originated from a cross-pollination made by the Inventor in November, 2001 in Venhuizen, The Netherlands of a proprietary selection of *Fuchsia×hybrida* identified as code number A 2504, not patented, as the female, or seed, parent with a proprietary selection of *Fuchsia×hybrida* identified as code number 1385-2, not patented, as the male, or pollen, parent. The new *Fuchsia* was discovered and selected by the Inventor as a single flowering plant within the progeny of the stated cross-pollination in a controlled environment in Venhuizen, The Netherlands during the summer of 2002.

Asexual reproduction of the new *Fuchsia* by terminal cuttings in a controlled environment in Venhuizen, The Netherlands since 2002, has shown that the unique features of this new *Fuchsia* are stable and reproduced true to type in successive generations.

SUMMARY OF THE INVENTION

The cultivar 'Kiefucor' has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kiefucor'. These characteristics in combination distinguish 'Kiefucor' as a new and distinct cultivar of *Fuchsia:*

1. Outwardly arching to trailing growth habit.
2. Freely branching plant habit.

3. White-colored flowers.
4. Freely and continuous flowering habit.

Plants of the new *Fuchsia* differ primarily from plants of the parent selections in flower coloration.

Plants of the new *Fuchsia* can also be compared to plants of the cultivar First Kiss, not patented. In side-by-side comparisons conducted in Venhuizen, The Netherlands, plants of the new *Fuchsia* and the cultivar First Kiss differed in the following characteristics:

1. Plants of the new *Fuchsia* flowered for a longer period of time and more continuously than plants of the cultivar First Kiss.
2. Flower color of plants of the new *Fuchsia* was white whereas flower color of plants of the cultivar First Kiss was white blushed with pink.
3. Plants of the new *Fuchsia* were more tolerant to high temperatures than plants of the cultivar First Kiss.

BRIEF DESCRIPTION OF THE PHOTOGRAPHS

The accompanying colored photographs illustrate the overall appearance of the new *Fuchsia,* showing the colors as true as it is reasonably possible to obtain in colored reproductions of this type. Colors in the photographs may differ slightly from the color values cited in the detailed botanical description which accurately describe the colors of the new *Fuchsia.*

The photograph at the bottom of the sheet comprises a side perspective view of a typical flowering plant of 'Kiefucor' grown in a container.

The photograph at the top of the sheet comprises a close-up of typical flowers and flower buds of 'Kiefucor'.

DETAILED BOTANICAL DESCRIPTION

The photographs and following observations, measurements and values describe plants grown in Lompoc, Calif., under commercial practice during the winter and early spring in a polycarbonate-covered greenhouse with day temperatures ranging from 18° C. to 24° C., night temperatures ranging from 16° C. to 18° C., and light levels ranging from about 4,000 to 8,000 foot candles. Plants were grown for about 19 weeks with one plant per 12.5-cm container. In the following description, color references are made to The Royal Horticultural Society Colour Chart, 1995 Edition, except where general terms of ordinary dictionary significance are used.

Botanical classification: *Fuchsia×hybrida* cultivar 'Kiefucor'.

Parentage:

*Female, or seed, parent.*—Proprietary selection of *Fuchsia×hybrida* identified as code number A 2504, not patented.

*Male, or pollen, parent.*—Proprietary selection of *Fuchsia×hybrida* identified as code number 1385-2, not patented.

Propagation:

*Type.*—By terminal cuttings.

*Time to produce a rooted young plant, summer.*—About three weeks at temperatures of 21° C.

*Time to produce a rooted young plant, winter.*—About four weeks at temperatures of 21° C.

*Root description.*—Fine, fibrous, white in color.

*Rooting habit.*—Freely branching; dense.

Plant description:

*Plant and growth habit.*—Initially upright, then outwardly spreading to trailing; dense and full plant form. Freely branching; about seven primary branches per plant and numerous secondary branches. Moderate to rapid growth rate.

*Plant height.*—About 22 cm.

*Plant diameter.*—About 39 cm by 53 cm.

Lateral branch description:

*Length.*—About 35 cm.

*Diameter.*—About 4 mm.

*Internode length.*—About 2.6 cm.

*Strength.*—Strong.

*Aspect.*—Initially upright to outwardly arching to trailing.

*Texture, immature.*—Pubescent; minute.

*Texture, mature.*—Woody; glabrous.

*Color, immature.*—145A tinted with 182B.

*Color, mature.*—199A.

Foliage description:

*Arrangement.*—Opposite, simple.

*Length.*—About 3.8 cm.

*Width.*—About 2 cm.

*Shape.*—Elliptic.

*Apex.*—Acute.

*Base.*—Acute.

*Margin.*—Entire with regular minute points.

*Texture, upper and lower surfaces.*—Smooth, glabrous.

*Venation pattern.*—Pinnate; arcuate.

*Color.*—Developing foliage, upper surface: 146A. Developing foliage, lower surface: 146B. Fully expanded foliage, upper surface: 147A; venation, 147C. Fully expanded foliage, lower surface: 147B; venation, 147B.

*Petiole.*—Length: About 1.3 cm. Diameter: About 1 mm. Texture, upper and lower surfaces: Smooth, glabrous. Color, upper and lower surfaces: 148B.

Flower description:

*Flower arrangement and habit.*—Single white-colored axillary flowers. Flowers initially upright and then pendulous. Flowers not fragrant. Freely flowering habit with potentially two flowers per leaf axil; at one time, about 16 open flowers and flower buds per lateral branch.

*Natural flowering season.*—In northern Europe, plants flower from early spring to fall; flowering continuous during this period. Flowers last about seven days on the plant. Flowers not persistent.

*Flower diameter.*—About 5.4 cm; corolla diameter, about 1.6 cm.

*Flower height.*—About 4.5 cm; corolla length, about 1.5 cm.

*Flower buds.*—Shape: Ovoid; elongate. Length: About 4.6 cm. Diameter: About 1.3 cm. Color: 157D.

*Petals.*—Arrangement: Four or five in a single whorl. Length: About 1.7 cm. Width: About 1.7 cm. Shape: Obovate with three rounded lobes at apex. Apex: Rounded; tri-lobed. Margin: Entire. Texture, upper and lower surfaces: Smooth, glabrous; velvety. Color: When opening, upper surface: 155B. When opening, lower surface: 155C. Fully opened, upper surface: 155C. Fully opened, lower surface: 155D.

*Sepals.*—Arrangement: Calyx star-shaped with four or five sepals fused at the base. Length: About 3.3 cm. Calyx tube length: About 9 mm. Width: About 1 cm. Calyx tube diameter: About 4 mm. Shape: Elliptic. Apex: Acuminate. Margin: Entire. Texture, upper and lower surfaces: Smooth, glabrous. Color: When opening, upper surface: 155C. When opening, lower surface: 155D. Fully opened, upper surface: 155C; towards the apex, 145A. Fully opened, lower surface: 155D.

*Peduncles.*—Length: About 2.8 cm. Diameter: About 1 mm. Angle: About 45° to 60° from vertical. Strength: Strong. Texture: Smooth, glabrous. Color: 146C.

*Reproductive organs.*—Stamens: Quantity: Eight per flower. Anther shape: Oblong. Anther size: About 2 mm by 3 mm. Anther color: 58D. Pollen amount: Moderate. Pollen color: 155A. Pistils: Quantity: One per flower. Pistil length: About 6 cm. Style length: About 5.2 cm. Style color: 155B. Stigma shape: Rounded. Stigma color: 160D. Ovary color: 144B. Seed/fruit: Seed and fruit development have not been observed on plants of the new *Fuchsia*.

Temperature tolerance: Plants of the new *Fuchsia* have been observed to tolerate temperatures from about 10° C. to about 35° C.

Pathogen/pest resistance: Plants of the new *Fuchsia* have not been observed to be resistant to pests and pathogens common to *Fuchsia*.

It is claimed:

1. A new and distinct *Fuchsia* plant named 'Kiefucor' as illustrated and described.

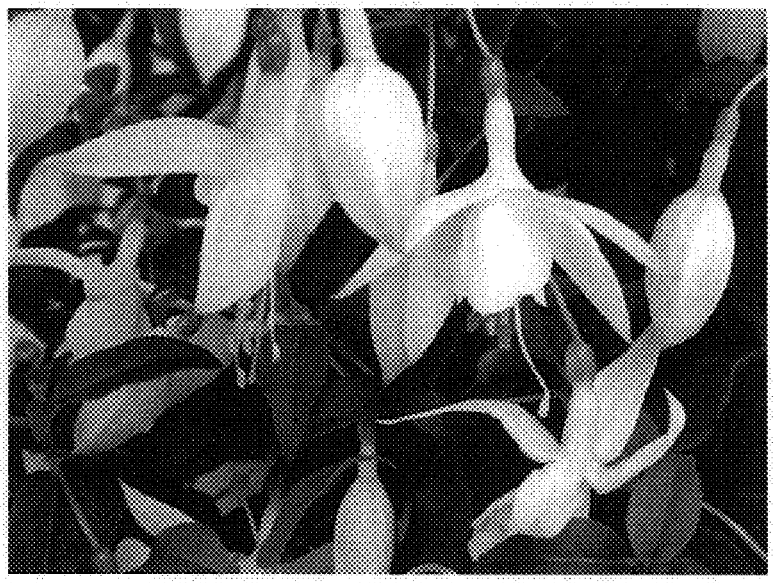
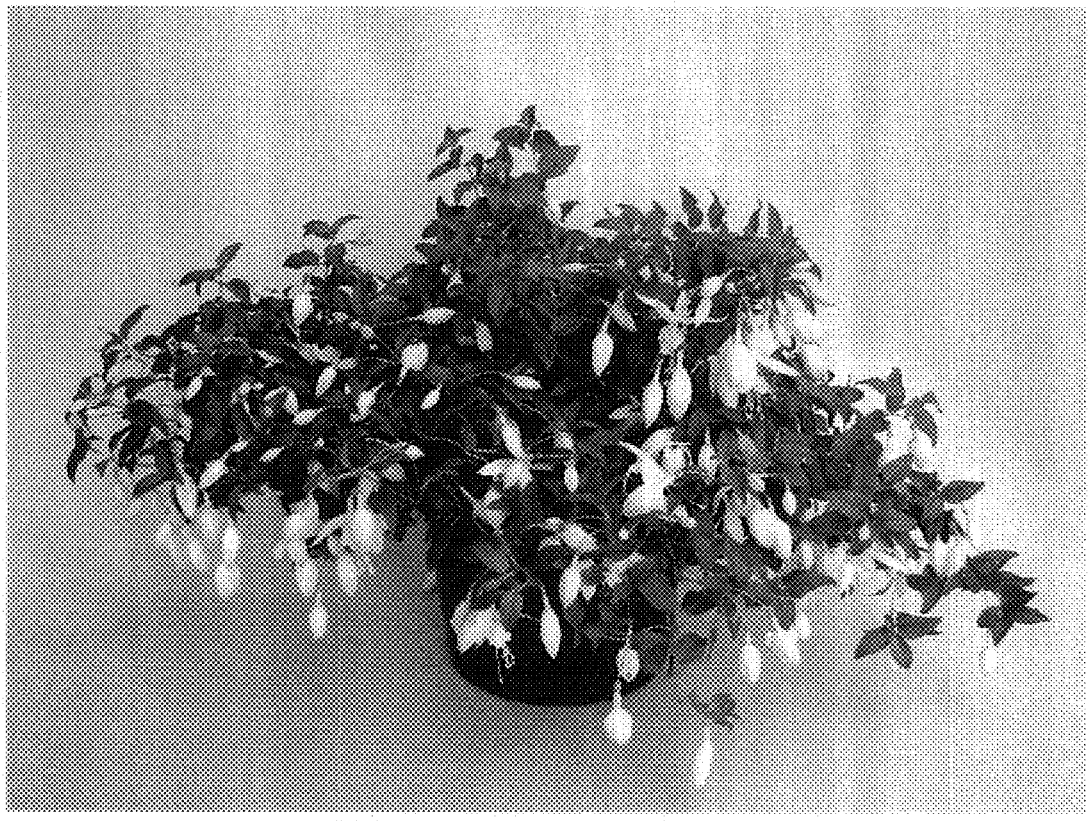

* * * * *